US012697444B2

(12) United States Patent
Hariu et al.

(10) Patent No.: US 12,697,444 B2
(45) Date of Patent: Aug. 4, 2026

(54) INJECTION NEEDLE

(71) Applicant: Kao Corporation, Tokyo (JP)

(72) Inventors: Wataru Hariu, Utsunomiya (JP);
Takatoshi Niitsu, Utsunomiya (JP);
Tomoya Nishimura, Tokyo (JP)

(73) Assignee: KAO CORPORATION, Tokyo (JP)

( * ) Notice: Subject to any disclaimer, the term of this
patent is extended or adjusted under 35
U.S.C. 154(b) by 386 days.

(21) Appl. No.: 18/568,445

(22) PCT Filed: Jun. 2, 2022

(86) PCT No.: PCT/JP2022/022541
§ 371 (c)(1),
(2) Date: Dec. 8, 2023

(87) PCT Pub. No.: WO2022/259959
PCT Pub. Date: Dec. 15, 2022

(65) Prior Publication Data
US 2024/0269395 A1     Aug. 15, 2024

(30) Foreign Application Priority Data

Jun. 9, 2021     (JP) ................................ 2021-096972
May 31, 2022     (JP) ................................ 2022-089295

(51) Int. Cl.
A61M 5/46          (2006.01)
A61M 37/00         (2006.01)
(52) U.S. Cl.
CPC ....... A61M 5/46 (2013.01); A61M 2037/0023
(2013.01)

(58) Field of Classification Search
CPC ............ A61M 5/46; A61M 2037/0023; A61M
2037/003; A61M 5/42; A61M 37/0015;
A61M 2037/0046; A61M 2037/0038
See application file for complete search history.

(56) References Cited

U.S. PATENT DOCUMENTS 5,250,067 A * 10/1993 Gelfer .................... A61H 39/00
606/189
6,183,434 B1     2/2001 Eppstein
(Continued)

FOREIGN PATENT DOCUMENTS

CN          106535980 A      3/2017
CN          112516451 A      3/2021
(Continued)

OTHER PUBLICATIONS

International Search Report and Written Opinion mailed on Aug. 30,
2022, received for PCT Application PCT/JP2022/022541, filed on
Jun. 2, 2022, 14 pages including English Translation.
(Continued)

*Primary Examiner* — Dung T Ulsh
(74) *Attorney, Agent, or Firm* — XSENSUS LLP

(57) ABSTRACT
An injection needle includes: protrusions that protrude from
a sheet base. The protrusions include a first protrusion
having an opening at a tip end portion and being hollow, a
second protrusion having no opening at a tip end portion;
and an insertion depth controller provided at an intermediate
position lower than a tip end position of the first protrusion
and higher than a surface of the sheet base. A difference in
height between the tip end position of the first protrusion and
a position of the insertion depth controller is preferably 1 μm
or more and 5 000 μm or less.

20 Claims, 13 Drawing Sheets

(56)  References Cited

U.S. PATENT DOCUMENTS

| | | |
|---|---|---|
| 2007/0004989 A1* | 1/2007 | Dhillon ............ A61B 5/150022 |
| | | 600/583 |
| 2011/0306853 A1 | 12/2011 | Black et al. |
| 2012/0245445 A1 | 9/2012 | Black et al. |
| 2015/0306363 A1 | 10/2015 | Meyer et al. |
| 2017/0120027 A1 | 5/2017 | Shiomitsu |
| 2018/0185624 A1 | 7/2018 | Ueno et al. |
| 2020/0001064 A1 | 1/2020 | Alary et al. |
| 2020/0001065 A1 | 1/2020 | Alary et al. |
| 2020/0269029 A1 | 8/2020 | Hamamoto et al. |
| 2020/0330739 A1 | 10/2020 | Atari et al. |
| 2021/0322745 A1 | 10/2021 | Agarwal et al. |
| 2022/0347449 A1 | 11/2022 | Alary et al. |

FOREIGN PATENT DOCUMENTS

| | | | |
|---|---|---|---|
| EP | 2957316 A1 | 12/2015 | |
| JP | 2007-037707 A | 2/2007 | |
| JP | 2009-061144 A | 3/2009 | |
| JP | 2017-038781 A | 2/2017 | |
| JP | 2021-023675 A | 2/2021 | |
| KR | 10-2020-0053472 A | 5/2020 | |
| KR | 10-2020-0085224 A | 7/2020 | |
| KR | 10-2021-0025601 A | 3/2021 | |
| WO | 2020/064085 A1 | 4/2020 | |
| WO | 2021/177317 A1 | 9/2021 | |

OTHER PUBLICATIONS

International Preliminary Report on Patentability mailed on Dec. 14, 2022, received for PCT Application PCT/JP2022/022541, filed on Jun. 2, 2022, 8 pages including English Translation.

* cited by examiner 31,32,33

Fig. 8
(a)
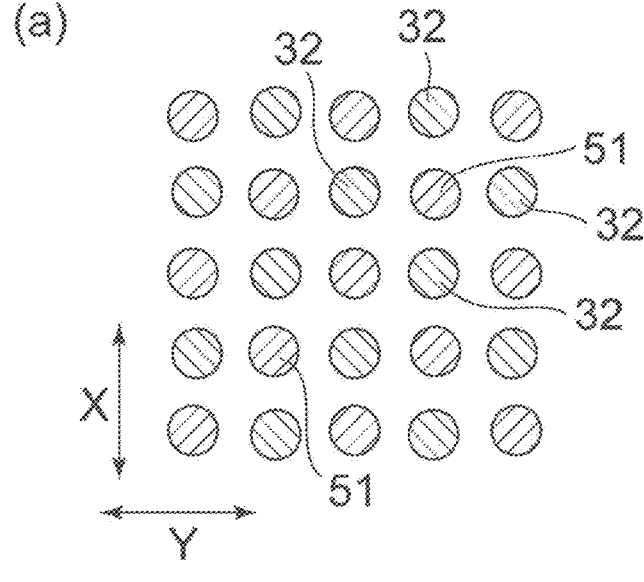
(b)
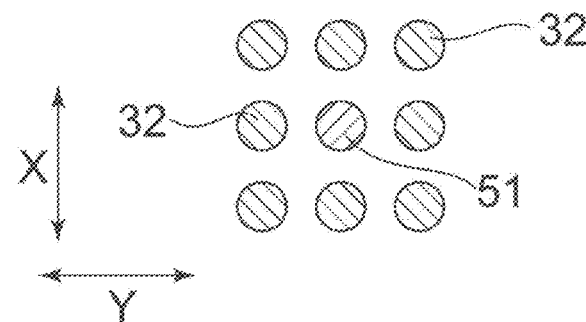
(c)
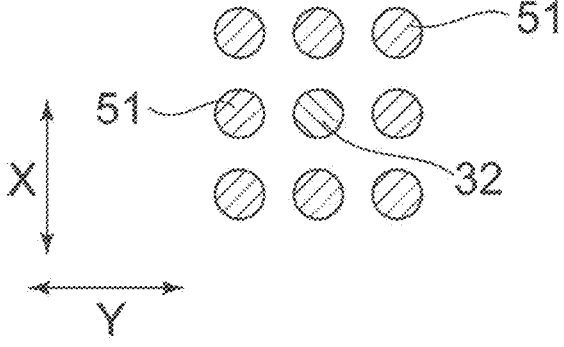

Fig. 11
(a)
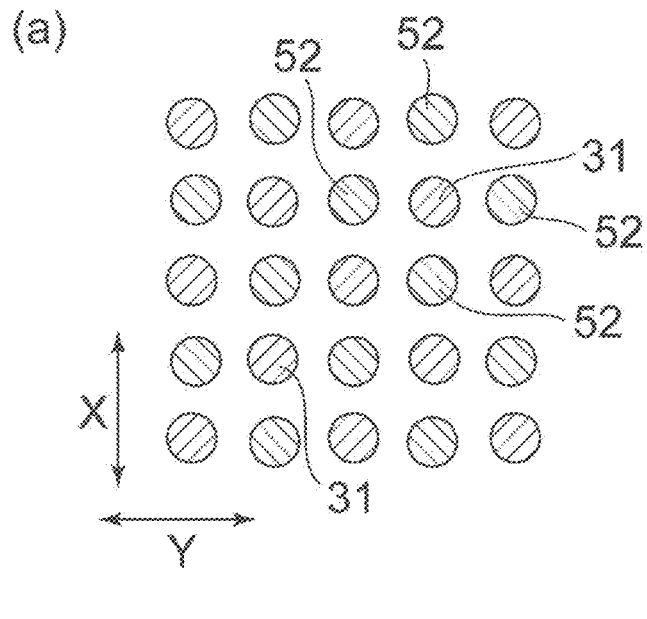
(b)
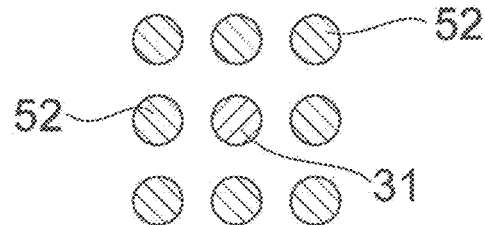
(c)
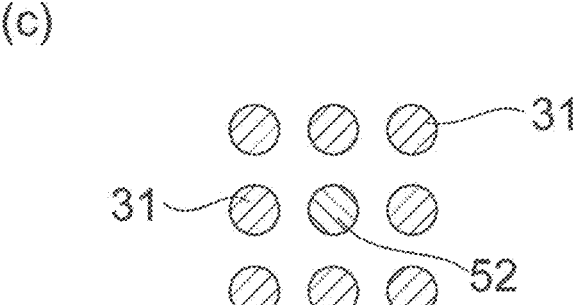

Fig. 12
(a)
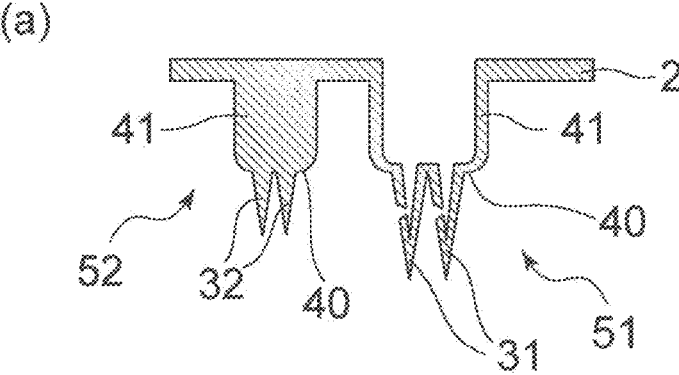
(b)
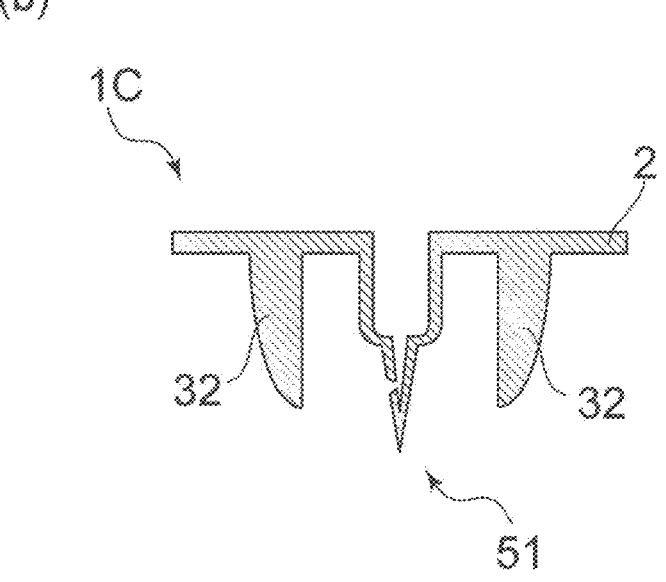

Fig. 13
(a)
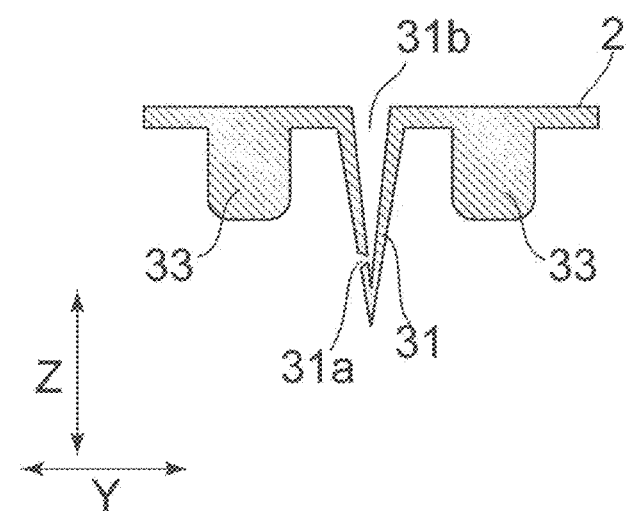
(b)
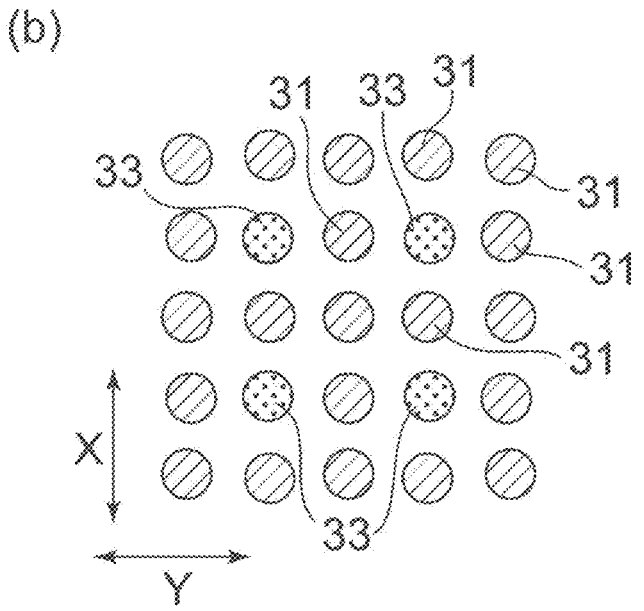

Fig. 14
(a)
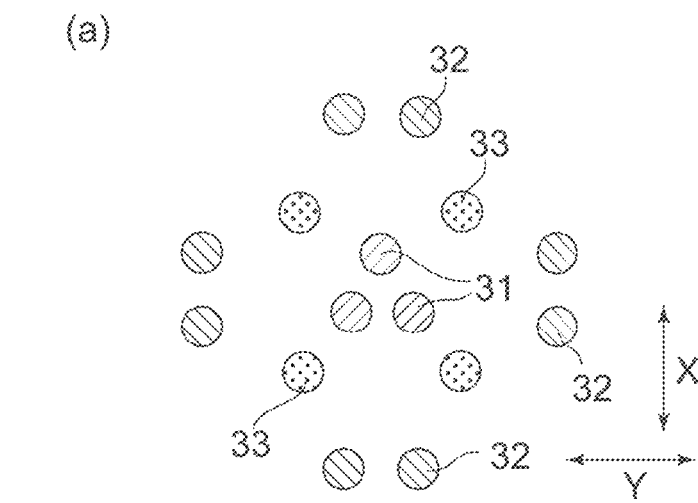
(b)
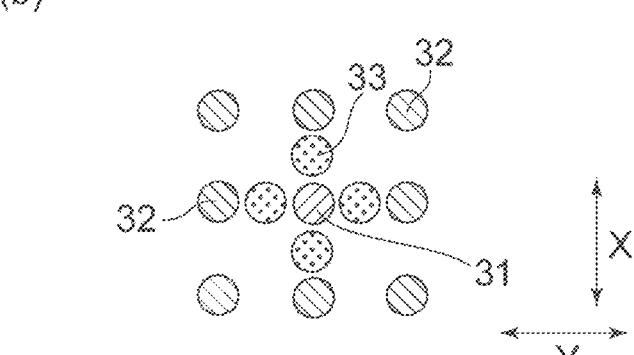
(c)
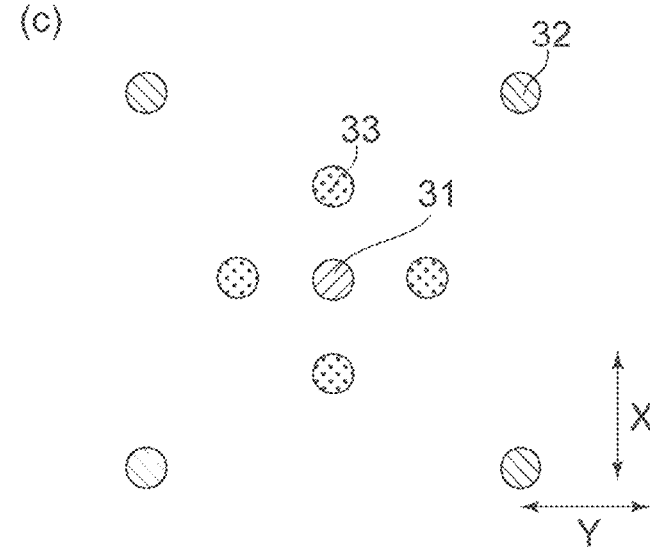

INJECTION NEEDLE

CROSS-REFERENCE TO RELATED APPLICATIONS

The present application is based on PCT filing PCT/JP2022/022541, filed Jun. 2, 2022, which claims priority from Japanese Patent Application Nos. 2021-096972, filed Jun. 9, 2021, and 2022-089295, filed May 31, 2022, the entire contents of each are incorporated herein by reference.

TECHNICAL FIELD

The present invention relates to an injection needle.

BACKGROUND ART

In recent years, in medical fields, cosmetic fields, and the like, attention has been paid to percutaneous absorption of drugs with the use of a liquid injection tool including fine needle-like protrusions, which are also called microneedles. With this liquid injection tool, it is possible to inject a liquid into a human body by inserting the microneedles into a relatively shallow layer of the skin such as the stratum corneum, which significantly reduces pain felt by the subject as compared with an ordinary syringe. Accordingly, attention has been paid to such a liquid injection tool as minimally-invasive liquid injection means.

Patent Literature 1 discloses a microprotrusion implement including a needle-like and hollow first protrusion formed to protrude from an upper surface, which is one surface of a base sheet having a circular shape in a plan view and a hollow second protrusion formed to protrude from the vicinity of the first protrusion on the upper surface of the base sheet and having a lower protrusion height than that of the first protrusion. In Patent Literature 1, when the first protrusion is inserted into the skin from the tip end side, the insertion of the first protrusion is stopped at a time when a tip end of the second protrusion in the vicinity of the first protrusion comes into contact with the surface of the skin, and the first protrusion is prevented from being inserted into a deeper site of the skin. An opening is formed at a tip end portion of the first protrusion, and a hollow portion of the first protrusion communicates with the outside through the opening. In Patent Literature 1, the tip end portion of the first protrusion is inserted into the skin, a liquid drug stored in the hollow portion of the first protrusion is injected into the skin from the opening of the tip end portion.

Patent Literature 2 discloses a microneedle sheet in which a plurality of groups of minute-sized needles protruding from the surface are formed. In Patent Literature 2, the groups of needles include a group of penetrating needles each having a through hole formed from a front surface side to a rear surface side and a group of dummy needles having no through hole.

CITATION LIST

Patent Literature

[Patent Literature 1] US2018/185624A1
[Patent Literature 2] WO2021/177317A1

SUMMARY OF INVENTION

The present invention provides an injection tool including protrusions protruding from a sheet base.

The injection needle of the present invention preferably includes, as the protrusions, a first protrusion having an opening at a tip end portion and being hollow, and a second protrusion having no opening at a tip end portion.

The injection needle of the present invention preferably includes an insertion depth controller provided at an intermediate position lower than a tip end position of the first protrusion and higher than a surface of the sheet base.

BRIEF DESCRIPTION OF DRAWINGS

FIGS. 8(a) to 8(c) are plan views schematically showing arrangement patterns of the protrusion in the injection needle shown in FIG. 6.

FIGS. 11(a) to 11(c) are plan views schematically showing arrangement patterns of the protrusion in the injection needle shown in FIG. 9.

FIG. 12(a) is a cross-sectional view schematically showing a modification of a composite first protrusion and a composite second protrusion: FIG. 12(b) is a cross-sectional view schematically showing a modification of a second protrusion.

FIG. 13(a) is a cross-sectional view in a thickness direction of an injection needle according to Comparative Example 1: FIG. 13(b) is a plan view schematically showing an arrangement pattern of a protrusion in the injection needle of Comparative Example 1.

FIG. 14(a) is a plan view schematically showing an arrangement pattern of a protrusion in an injection needle of Example 5: FIG. 14(b) is a plan view schematically showing an arrangement pattern of a protrusion in an injection needle of Example 6; and FIG. 14(c) is a plan view schematically showing an arrangement pattern of a protrusion in an injection needle of Example 7.

DESCRIPTION OF EMBODIMENTS

Figure 1:
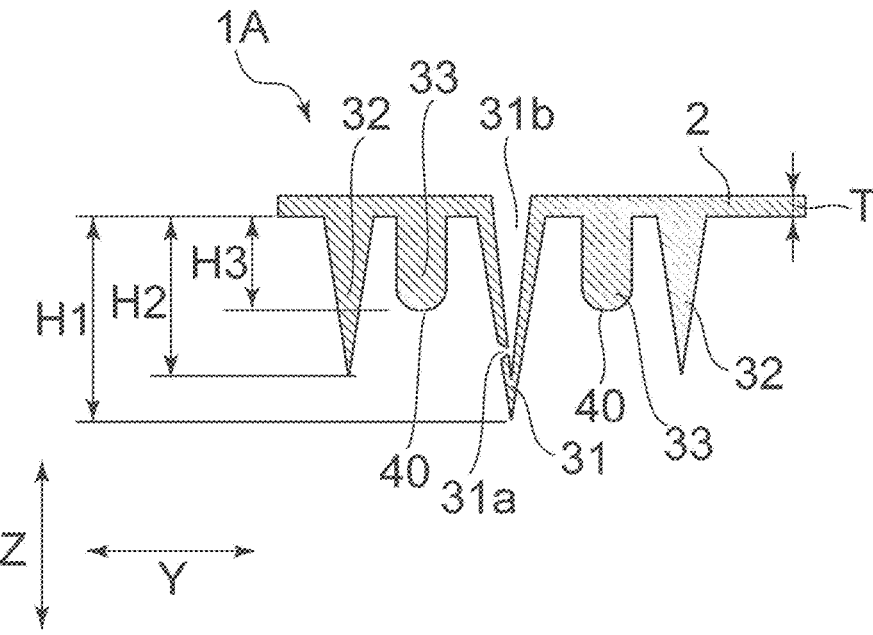
FIG. 1 is a cross-sectional view in a thickness direction of an injection needle according to a preferred embodiment of the present invention.

In the microprotrusion implement disclosed in Patent Literature 1, the protrusions of the microprotrusion implement include the first protrusion having a hollow and an opening and the second protrusion having the lower protrusion height than the first protrusion. Only the first protrusion is inserted into the skin. Further the second protrusion having the lower protrusion height than the first protrusion functions as a stopper that restricts the insertion depth of the first protrusion. For this reason, in such a microprotrusion implement of Patent Literature 1, a blood flow promoting effect caused by the protrusion being pressed against the skin or inserted into the skin is limited, and there is room for improvement. In particular, only the first protrusion is disclosed as a protrusion capable of stimulating the skin, but there is no disclosure to increase the density of the protrusions or to uniformly impart a blood flow promoting effect over a wide range.

In Patent Literature 2, there is no disclosure to control the insertion depth of the group of penetrating needles and the group of dummy needles.

The present invention relates to an injection needle capable of controlling a depth of insertion into a skin, injecting a liquid, and effectively promoting a blood flow.

The present invention will be described below with reference to preferred embodiments.

An injection needle 1A of the present invention has a protrusion protruding from a sheet base 20.

The injection needle 1A of the present invention typically has a flat sheet-like shape as a whole, and has a sheet base 2 and a plurality of protrusions protruding from one surface of the sheet base 2.

The injection needle 1A of the present invention typically has a protrusion arrangement region in which the protrusions are arranged in a state of being distributed in a plane direction. A shape of the protrusion arrangement region can be any shape of a quadrangular shape such as square or rectangular shape, a circular shape, an elliptical shape, a pentagonal shape, and a polygonal shape such as a hexagonal shape.

The protrusions of the injection needle 1A preferably include a first protrusion 31 having an opening 31a at a tip end portion and having a hollow, a second protrusion 32 having no opening at a tip end portion, and a third protrusion 33 having a lower height than any of the first protrusion 31 and the second protrusion 32. The first protrusion 31 is a microprotrusion having a hollow portion 31b, a so-called microneedle.

The second protrusion 32 and the third protrusion 33 may be hollow, or may be solid having no spaces inside. In the first embodiment, the second protrusion 32 and the third protrusion 33 are solid. Since the second protrusion 32 and the third protrusion 33 are solid, it is possible to reduce the amount of drugs remaining in the injection needle 1A when the drug is injected from the injection needle 1A of the present invention.

Further, preferably, the third protrusion 33 has a tip end surface of a flat shape, that is, a straight line shape extending in a horizontal direction, or is formed by a curved line projected in a protruding direction of the third protrusion.

The injection needle of the present invention preferably includes an insertion depth controller 40 at an intermediate position that is a position lower than a tip end position of the first protrusion 31 and higher than the surface of the sheet base 20. Typically, the tip end surface of the third protrusion 33 is the insertion depth controller 40. Such an example is shown in FIG. 1.

The insertion depth controller 40 controls an insertion depth of the first protrusion 31. The insertion depth controller 40 is preferably located at a position lower than the tip end position of the second protrusion 32.

In the injection needle 1A of the present invention, a plurality of second protrusions 32 are preferably formed around one first protrusion 31. These second protrusions 32 preferably have the same distance from the first protrusion 31.

In the injection needle 1A of the present invention, a plurality of third protrusions 33 are preferably formed around one first protrusion 31. These third protrusions 33 preferably have the same distance from the first protrusion 31.

Figure 2:
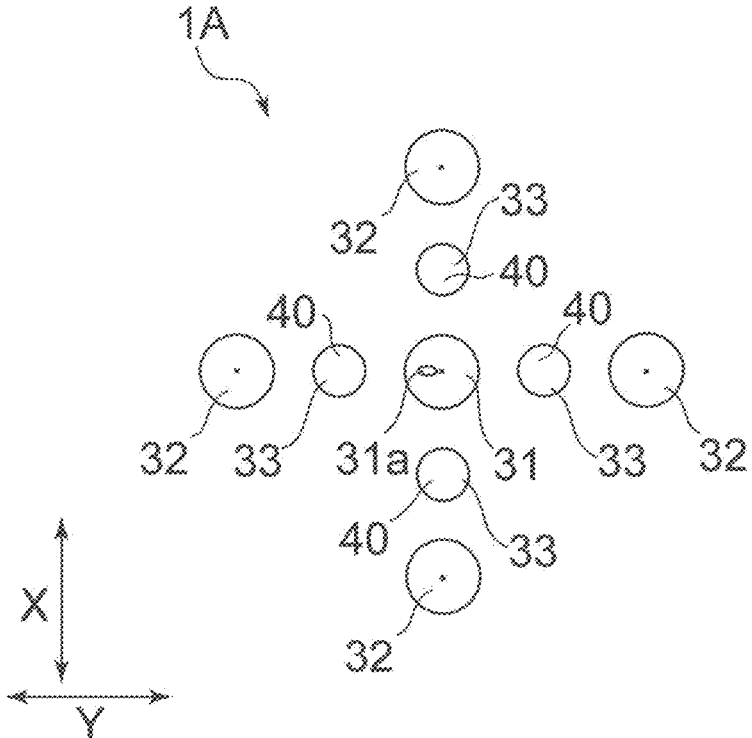
FIG. 2 is a plan view of the injection needle shown in FIG. 1.

More specifically, preferably, a pair of second protrusions 32, 32 are arranged with the first protrusion 31 interposed therebetween in a first direction X, and a pair of second protrusions 32, 32 are arranged with the first protrusion 31 interposed therebetween in a second direction Y orthogonal to the first direction X. Further, preferably, a pair of third protrusions 33, 33 are arranged with the first protrusion 31 interposed therebetween in the first direction X, and a pair of third protrusions 33, 33 are arranged with the first protrusion 31 interposed therebetween in the second direction Y. The third protrusion 33 is preferably arranged between the first protrusion 31 and the second protrusion 32. Such an example is shown in FIG. 2. The position of the second protrusion 32 and the position of the third protrusion 33 may be reversed. In other words, the second protrusion 32 may be arranged between the first protrusion 31 and the third protrusion 33.

In the injection needle 1A of the present invention, a plurality of unit arrangement patterns are continuous in the first direction X and the second direction Y in which the first protrusion 31, the second protrusion 32, and the third protrusion 33 are arranged in a predetermined positional relationship such that the second protrusion 32 is shared with the adjacent unit arrangement pattern.

In the injection needle 1A of the present invention, typically, the first protrusion 31 and the second protrusion 32 have a conical shape, and the third protrusion 33 has a columnar shape. More typically, the plurality of second protrusions 32 have the same shape and size, and the plurality of third protrusions 33 also have the same shape and size.

The injection needle 1A preferably contains a thermoplastic resin. Specifically, a base constituting the injection needle preferably contains a thermoplastic resin. Typically, the injection needle 1A is preferably formed in a manner that the base sheet containing the thermoplastic resin is plastically deformed by heating. A method of heating the base sheet may be a method of heating only a part of the base sheet, or a method of heating the entire base sheet. An example of the method of heating only a part of the base sheet and plastically deforming the base sheet may include a method of inserting a processing needle into a position where the protrusions are to be formed on the base sheet while applying ultrasonic vibration, or a method of inserting the heated processing needle into a position where the protrusions are to be formed on the base sheet. An example of the method of heating the entire base sheet and plastically deforming the base sheet may include a method of inserting a processing needle into a position where the protrusions are to be formed on the base sheet while heating the entire base sheet with a heating instrument such as a heater.

In order to make the second protrusion 32 and the third protrusion 33 solid, for example, a hollow portion of the hollow second protrusion or third protrusion formed by inserting the processing needle into the base sheet may be filled with a resin for forming the protrusions or another resin.

In the injection needle 1A of the present invention, the first protrusion 31 preferably includes an opening 31a. Thus, the injection needle 1A of the present invention serves as a liquid injection tool that can be used for percutaneous absorption of liquids such as drugs.

Typically, the opening 31a is formed at the tip end portion of the first protrusion 31, and the hollow portion 31b of the first protrusion 31 communicates with the outside through the opening 31a. The opening 31a is a through hole that penetrates the sheet base 2, which forms the first protrusion 31, in a thickness direction, and is preferably located at the tip end portion of the first protrusion 31 having the conical shape. The hollow portion 31b of the first protrusion 31 functions as a reservoir portion or a passage for a liquid discharged to the outside from the opening 31a. Here, the tip end portion of the first protrusion 31 means a region closer to the tip end from the intermediate position of a protrusion height H1 from the surface of the sheet base 2 to the tip end of the first protrusion 31.

When the injection needle 1A is used for percutaneous absorption of a drug, the tip end portion of the first protrusion 31 is inserted into a skin S, and a liquid drug L stored in the hollow portion 31b of the first protrusion 31 is injected into the skin S from the opening 31a of the tip end portion. As described above, the hollow portion 31b of the first protrusion 31 typically functions as a reservoir portion of the drug in a case where a drug is not supplied from the outside.

In a case where a drug is supplied from the outside, for example, when a drug feeder (not shown) such as an applicator is used in combination with the injection needle 1A, the hollow portion 31b functions as a passage of the drug. The drug feeder may be formed in such a manner that a sheet-like member is arranged on a back surface side of the injection needle 1A and a drug accommodating space is formed between the back surface of the injection needle 1A and the sheet-like member, and may feed the drug to the first protrusion 31 by pressing the sheet-like member (see a paragraph in JP 2020-096790 A).

The injection needle 1A preferably includes the second protrusion 32 in addition to the first protrusion 31.

In a case where a height H2 of the second protrusion 32 is higher than a height H3 of the insertion depth controller 40, when the injection needle 1A is pressed against the skin and the first protrusion 31 is inserted into the skin from the tip end side, the second protrusion 32 is also inserted into the skin. When the second protrusion 32 is inserted into the skin, the second protrusion 32 stimulates the skin and exerts a blood flow promoting action. Therefore, with the injection needle 1A having such a configuration, the liquid can be injected into the skin by the first protrusion 31, and the blood flow can be promoted by the second protrusion 32. Unlike the case where the protrusions included in the microprotrusion implement are only the first protrusions capable of injecting the liquid into the skin as in the microprotrusion implement disclosed in Patent Literature 1, the injection needle 1A can widely stimulate the skin using both the first protrusion 31 and the second protrusion 32. For this reason, unlike the case of only the first protrusions are increased for the purpose of widely stimulating the skin in the microprotrusion implement disclosed in Patent Literature 1, even when there are protrusions not partially inserted into the skin when the injection needle 1A is applied to the skin, the protrusions are not always the first protrusions having an opening, and thus it is possible to reduce the probability of liquid leakage.

When the injection needle 1A is pressed against the skin, the second protrusion 32 may only be pressed against the skin without being inserted into the skin. Typically, this is a case where the height H2 of the second protrusion 32 is equal to the distance H3 from the surface of the sheet base 2 to the insertion depth controller 40. Even in this case, the second protrusion 32 can stimulate the skin and exert the blood flow promoting action.

Further, the injection needle 1A preferably includes the insertion depth controller 40 in addition to the first protrusion 31 and the second protrusion 32. As described above, in the injection needle 1A, the tip end surface of the third protrusion 33 is preferably the insertion depth controller 40. When the first protrusion 31 and the second protrusion 32 are inserted into the skin from the tip end side, the insertion depth controller 40 comes into contact with the surface of the skin. Then, the insertion of the first protrusion 31 and the second protrusion 32 is stopped, and the first protrusion 31 and the second protrusion 32 are prevented from being inserted into a deeper site of the skin. In other words, the insertion depth controller 40 functions as a stopper that restricts the insertion depth of the first protrusion 31 and the second protrusion 32.

Figure 3:
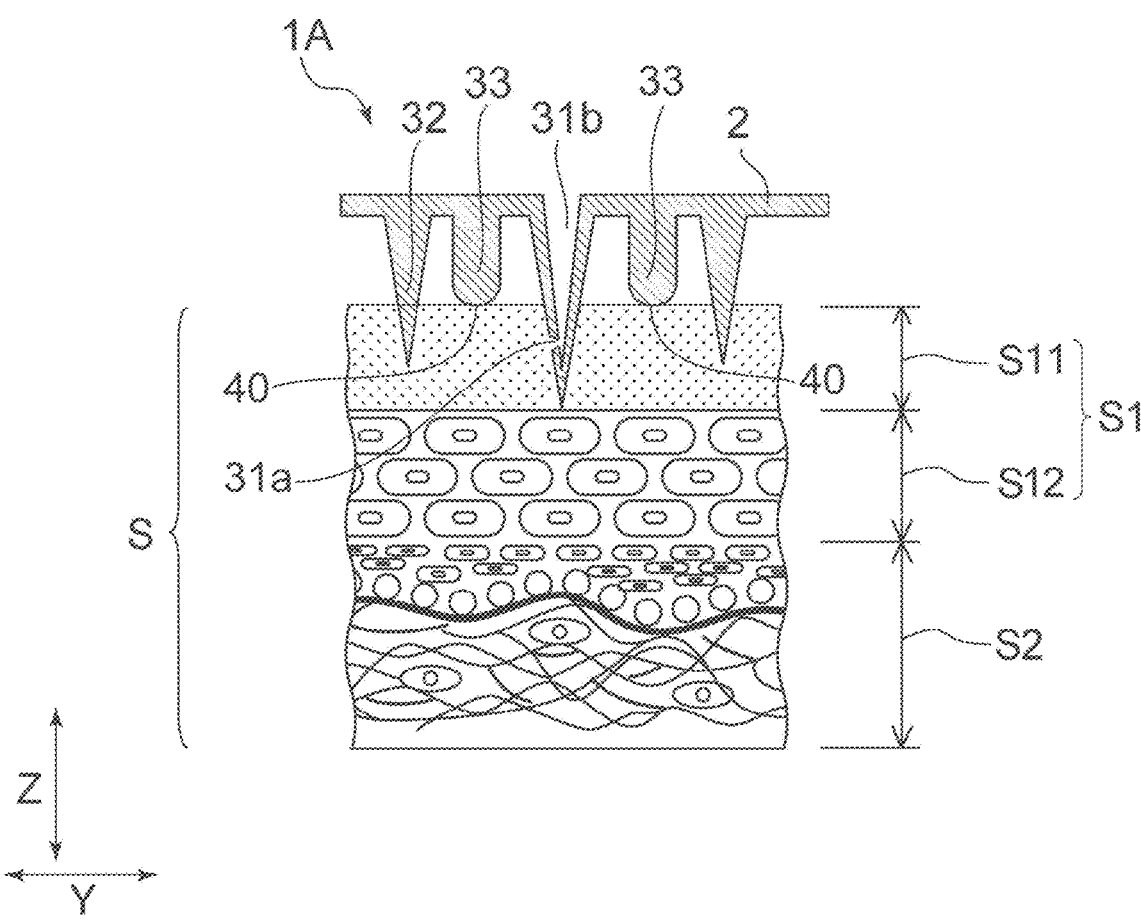
FIG. 3 is a diagram schematically showing a use state of the injection needle shown in FIG. 1, and a diagram showing a state in which a first protrusion of the injection needle is inserted into a stratum corneum of a skin and an insertion depth controller is in contact with a surface of the skin without being inserted into the skin.

An example having such a configuration is shown in FIG. 3.

The presence or absence of the blood flow promoting effect can be determined by various known methods and can be determined, for example, by whether a flare reaction occurs on the skin or by visualization of blood flow distribution with laser speckle flowgraphy (LSFG).

As described above, the injection needle 1A enables percutaneous absorption of the drug at a desired depth of the skin as the insertion depth of each of the first protrusion 31 and the second protrusion 32 into the skin is controllable, and also enables effective promotion of the blood flow. For this reason, with the injection needle 1A, the insertion depth of the first protrusion 31 is adjusted according to the type of the drug, and thus the effect of the drug can be maximized. In addition, the insertion depth of the second protrusion 32 is adjusted according to the intended degree of the blood flow promoting action, and thus the blood flow promoting action can be effectively generated.

Further, the first protrusion 31 and the second protrusion 32 are inserted into a stratum corneum S11, which is a surface layer of the skin S or a layer S12 located inner than the stratum corneum. However they are inhibited from being inserted into a dermis S2 and a hypodermic tissue U which is a site deeper than the skin S. Thereby a pain caused by the percutaneous absorption can be significantly reduced as compared with the syringe according to the related art. Generally, the skin S includes an epidermis S1 including the stratum corneum S11 constituting the surface layer of the skin S, the dermis S2 located inner than the epidermis S1, and the hypodermic tissue (not shown) located inner than the dermis S2. The layer S12 located inner than the stratum corneum S11 in the epidermis S1 typically includes stratum granulosum, stratum spinosum, and stratum basale in the order of proximity to the stratum corneum S11, and dermis S2 is located inside the stratum basale.

When percutaneous absorption of a drug is performed using a syringe equipped with an injection needle without the insertion depth controller 40, a person into whom the injection needle is inserted has to bear a pain caused by the insertion of the injection needle since the injection needle is inserted into the site S12, which is located inner than the stratum corneum beyond the stratum corneum, or the dermis S2, or even into the hypodermic tissue. However, with the injection needle 1A, it is possible to perform the percutaneous absorption of the drug and to promote the blood flow while reducing the pain felt by the person into whom the injection needle is inserted.

From the viewpoint of minimal-invasive percutaneous absorption and reduction of pain, the insertion depth controller 40 preferably controls the tip ends of the first protrusion 31 and the second protrusion 32 so as not to reach the dermis and hypodermic tissue U, and further preferably can control the tip ends thereof so as not to reach the site S12 located inner than the stratum corneum. Since the insertion depths of the first protrusion 31 and the second protrusion 32 coincide with distances in a height direction Z between the respective tip ends of the first protrusion 31 and the second protrusion 32 and the insertion depth controller in the vicinity thereof, the above-described effect can be more reliably achieved by appropriate adjustment of the distances in the height direction Z. The "minimal-invasion" in the present invention means a state where when the injection needle is pressed against the skin, the stratum corneum and the site located inner than the stratum corneum are damaged, but the dermis and the hypodermic tissue are not damaged.

In the injection needle 1A of the present invention, roles of the first protrusion 31 and the second protrusion 32 are different, wherein the blood flow promoting effect is provided by the second protrusion 32 and the blood flow promoting effect and the injection of the liquid are provided by the first protrusion 31. Thus, the injection amount of the liquid can be efficiently saved compared with a case where a large number of protrusions capable of injecting the liquid are provided for the purpose of obtaining the blood flow promoting effect. In particular, when the liquid is fed from one reservoir portion of a drug to the plurality of protrusions capable of injecting the liquid, the degree of insertion into the skin tends to differ depending on each protrusion. With the injection needle 1A of the present invention, the drug can be injected uniformly preventing leakage and the hypodermic depth at which injection is made can be made uniform. Further, the injection range of the liquid can also be set to the minimum but effective range enough to inject. The second protrusion 32 serves as a guide/indicator for vertically inserting the injection needle 1A into the skin. The second protrusion 32 also has an effect to facilitate the insertion of the first protrusion 31 by restraining the deformation of the skin. In addition, for example, when the injection needle 1A is not perpendicular to the skin inevitably at the time of using it, the injection needle 1A is inserted slanted to the skin. Thus, the protrusion arranged on the outer periphery of the injection needle 1A may not be sufficiently inserted into the skin depending on the direction. However, when the second protrusion is arranged on an outer periphery of the injection needle 1A, the first protrusion arranged on an inner periphery of the injection needle 1A may be sufficiently inserted into the skin and the drug can be injected without leaking into the skin S. In other words, the injection needle 1A of the present invention can easily control the injection amount of the liquid and the injection range of the liquid, and can efficiently inject the drug.

From the viewpoint of significantly reducing the pain caused by the percutaneous absorption or reliably injecting the drug from the first protrusion 31 into the skin S, a difference in height between the tip end position of the first protrusion 31 and the position of the insertion depth controller 40 is preferably 1 μm or more, and further preferably 5 μm or more. The difference in height is, that is, a difference $H1-H3$ between the protrusion height $H1$ of the first protrusion 31 and the distance $H3$ from the surface of the sheet base 2 to the insertion depth controller 40.

Further, the difference $H1-H3$ is preferably 5 000 μm or less, and further preferably 4 000 μm or less, from the viewpoint of not damaging the dermis more than necessary.

Further, the difference $H1-H3$ is preferably 1 μm or more and 5 000 μm or less, and more preferably 5 μm or more and 4 000 μm or less.

From the viewpoint of significantly reducing a pain associated with the blood flow promoting effect due to the second protrusion 32, preventing a poor insertion of the second protrusion due to elasticity of the skin, and sufficiently inserting the second protrusion into the skin, a protrusion height $H2$ of the second protrusion 32 is equal to or more than the distance $H3$ from the surface of the sheet base 2 to the insertion depth controller 40, that is, preferably $H2>H3$, and more preferably $H2>H3$.

From the same viewpoint, a difference $H2-H3$ is preferably 0 or more, more preferably 100 μm or more, and even more preferably 400 μm or more.

Further, a difference $H2-H3$ is preferably 5 000 μm or less, and more preferably 4 000 μm or less, from the viewpoint of not damaging the skin more than necessary.

Further, the difference $H2-H3$ is preferably 0 or more and 5 000 μm or less, more preferably 100 μm or more and 5 000 μm or less, and even more preferably 400 μm or more and 4 000 μm or less.

From the viewpoint of further reliably exerting the blood flow promoting effect and of ensuring the insertion of the first protrusion 31 to prevent drug leakage caused by insufficient insertion, the first protrusion 31 preferably has a height higher than a height of the second protrusion 32. More specifically, a difference $H1-H2$ between the protrusion height $H1$ of the first protrusion 31 and the protrusion height $H2$ of the second protrusion 32 is preferably 1 μm or more, and more preferably 5 μm or more.

Further, the difference $H1-H2$ is preferably 5 000 μm or less, and more preferably 4 000 μm or less, from the viewpoint of facilitating compatibility between the ease of injection of the liquid and the blood flow promoting effect.

Further, the difference $H1-H2$ is preferably 1 μm or more and 5 000 μm or less, and more preferably 5 μm or more and 4 000 μm or less.

The protrusion height $H1$ of the first protrusion 31 is preferably 10 μm or more, and more preferably 20 μm or more, from the viewpoint of preventing the inhibition of insertion due to the deformation of the skin when the first protrusion 31 is pressed against the skin, improving a puncturability, and reliably injecting the drug into the skin S.

Further, the protrusion height $H1$ of the first protrusion 31 is preferably 5 000 μm or less, and more preferably 4 000 μm or less, from the viewpoint of minimal-invasion.

Further, the protrusion height $H1$ of the first protrusion 31 is preferably 10 μm or more and 5 000 μm or less, and more preferably 20 μm or more and 4 000 μm or less, from the viewpoint of achieving both improved puncturability and minimal-invasiveness.

The protrusion height $H2$ of the second protrusion 32 is preferably 10 μm or more, and more preferably 20 μm or more, from the viewpoint of stimulating the skin by pressing against the skin and promoting the blood flow.

Further, the protrusion height $H2$ of the second protrusion 32 is preferably 5 000 μm or less, and more preferably 4 000 μm or less, from the viewpoint of minimal-invasion.

Further, the protrusion height H2 of the second protrusion 32 is preferably 10 μm or more and 5 000 μm or less, and more preferably 20 μm or more and 4 000 μm or less, from the viewpoint of improving blood flow promotion.

The distance H3 from the surface of the sheet base 2 to the insertion depth controller 40 is preferably 5 μm or more, and more preferably 10 μm or more.

Further, the distance H3 is preferably 4 000 μm or less, and more preferably 3 000 μm or less, from the viewpoint of improving the puncturability of the first protrusion 31.

Further, the distance H3 is preferably 5 μm or more and 4 000 μm or less, and more preferably 10 μm or more and 3 000 μm or less.

In reality, the tip end diameter of the first protrusion 31 is preferably 1 μm or more, and more preferably 5 μm or more.

Further, the tip end diameter of the first protrusion 31 is preferably 300 μm or less, and more preferably 100 μm or less, from the viewpoint of preventing the inhibition of puncture due to the elasticity of the skin.

Further, the tip end diameter of the first protrusion 31 is preferably 1 μm or more and 300 μm or less, and more preferably 5 μm or more and 100 μm or less.

The tip end diameter of the second protrusion 32 is preferably 1 μm or more, and more preferably 5 μm or more.

Further, the tip end diameter of the second protrusion 32 is preferably 300 μm or less, and more preferably 200 μm or less, from the viewpoint of improving the blood flow promoting effect.

Further, the tip end diameter of the second protrusion 32 is preferably 1 μm or more and 300 μm or less, and more preferably 5 μm or more and 200 μm or less.

The tip end diameter of the third protrusion 33 is preferably 2 μm or more, and more preferably 10 μm or more, from the viewpoint of acting as a stopper that prevents the first protrusion 31 from being inserted more than necessary.

The tip end diameter of the second protrusion 32 may be equal to or larger than the tip end diameter of the first protrusion 31, or may be equal to or smaller than the tip end diameter of the first protrusion 31.

Further, the tip end diameter of the third protrusion 33 is preferably 2 000 μm or less, and more preferably 100 μm or less, from the viewpoint of improving the degree of density of the first protrusion and the second protrusion.

Further, the tip end diameter of the third protrusion 33 is preferably 2 μm or more and 2 000 μm or less, and more preferably 10 μm or more and 100 μm or less.

The tip end diameter of the third protrusion 33 may be equal to or larger than the tip end diameter of the first protrusion 31, or may be equal to or smaller than the tip end diameter of the first protrusion 31.

The tip end diameters of the first to third protrusions 31 to 33 are measured by the following method.

[Method of Measuring Tip End Diameter of Protrusion on Injection Needle]

Figure 4:
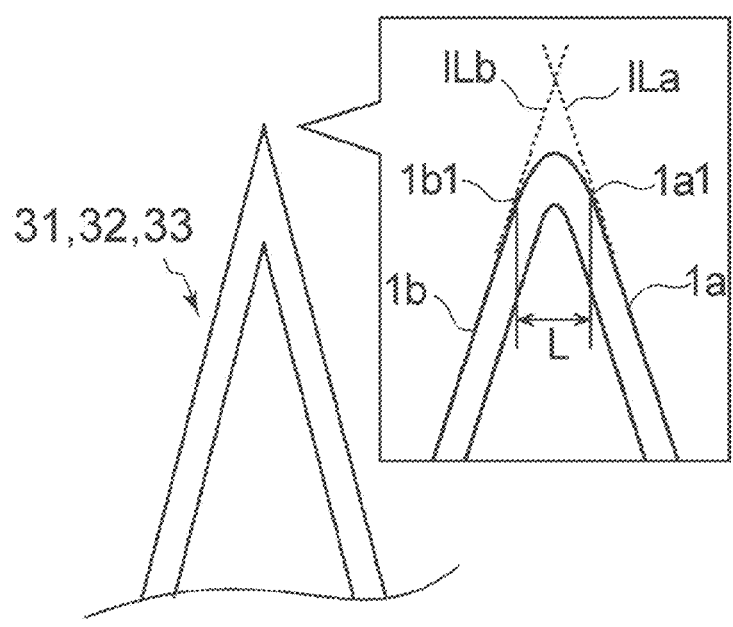
FIG. 4 is an explanatory diagram showing a method of measuring a tip end diameter of the protrusion in the injection needle.

The tip end portion of the protrusion (first protrusion 31, second protrusion 32, or third protrusion 33) to be measured is observed using a scanning electron microscope (SEM) or a microscope as shown in FIG. 4. Next, as shown in FIG. 4, a virtual straight line ILa extends along a straight line on one lateral side 1a of both lateral sides 1a and 1b, and a virtual straight line ILb extends along a straight line on the other lateral side 1b. Then, on the tip end side, a first tip end point 1a1 is obtained as a point where one lateral side 1a is separated from the virtual straight line ILa, and a second tip end point 1b1 is obtained as a point where the other lateral side 1b is separated from the virtual straight line ILb. A length L of a straight line connecting the first tip end point 1a1 and the second tip end point 1b1 obtained in this way is measured. The measured length of the straight line is defined as a tip end diameter of the protrusion to be measured.

The first protrusion 31 preferably has the opening 31a at the tip end portion as described above. Then, the opening 31a is preferably not formed at the tip end of the first protrusion 31, but is formed at the side surface of the first protrusion 31. When the opening 31a is formed at such a position, the opening 31a is not easily crushed when the first protrusion 31 is inserted into the skin, and the liquid such as a drug can be stably fed into the inside of the skin from the injection needle 1A through the opening 31a.

The first protrusion 31 can be arranged at an arbitrary position in the protrusion arrangement region, but is preferably located at an inner position than the second protrusion 32 in the protrusion arrangement region, that is, on a center side of the protrusion arrangement region. Thus, when the injection needle 1A is pressed against the skin, a load is easily applied to the first protrusion 31, and the first protrusion 31 is easily inserted into the skin. In addition, the first protrusion 31 is preferably surrounded by the second protrusion 32. Thus, the inserted site of the first protrusion 31 is surrounded by a region where blood flow is promoted and immunity-induced by the weak stimulation of the second protrusion 32, and it is considered that a medicinal effect of the drug injected by the first protrusion 31 can be improved. Further, when the injection needle 1A is used, the injection needle 1A may not be perpendicular to the skin inevitably and may be inserted slantly into the skin. In this case, since the first protrusion 31 is located on the center side, the first protrusion 31 can be stably inserted into the skin regardless of the direction in which the injection needle 1A is slanted with respect to the skin, and the leakage of the drug can be effectively prevented when the insertion is insufficient. From the viewpoint of making these effects more remarkable, the second protrusion 32 is preferably located on the outermost side of the protrusion arrangement region.

An arrangement pattern of the first protrusion 31, the second protrusion 32, and the third protrusion 33 is not particularly limited.

From the viewpoint of accurately controlling the insertion depth, an array (hereinafter, referred to as "first array") is preferable in which either or both of the first protrusion 31 and the second protrusion 32 are arranged between a pair of third protrusions 33 adjacent to each other. An array (hereinafter, referred to as "second array") is also preferable in which either or both of the first protrusion 31 and the second protrusion 32 having no insertion depth controller are arranged between the composite protrusions (composite first protrusion 51 or composite second protrusion 52) having the insertion depth controller.

The protrusion located between the third protrusions 33 in the first array or the protrusion located between the composite protrusions in the second array may be any one of only the first protrusion 31, only the second protrusion 32, or both the first protrusion 31 and the second protrusion 32. The number of protrusions located between the third protrusions 33 or the composite protrusions is preferably 1 or more and 4 or less, and more preferably 1 or 2.

Figure 5:
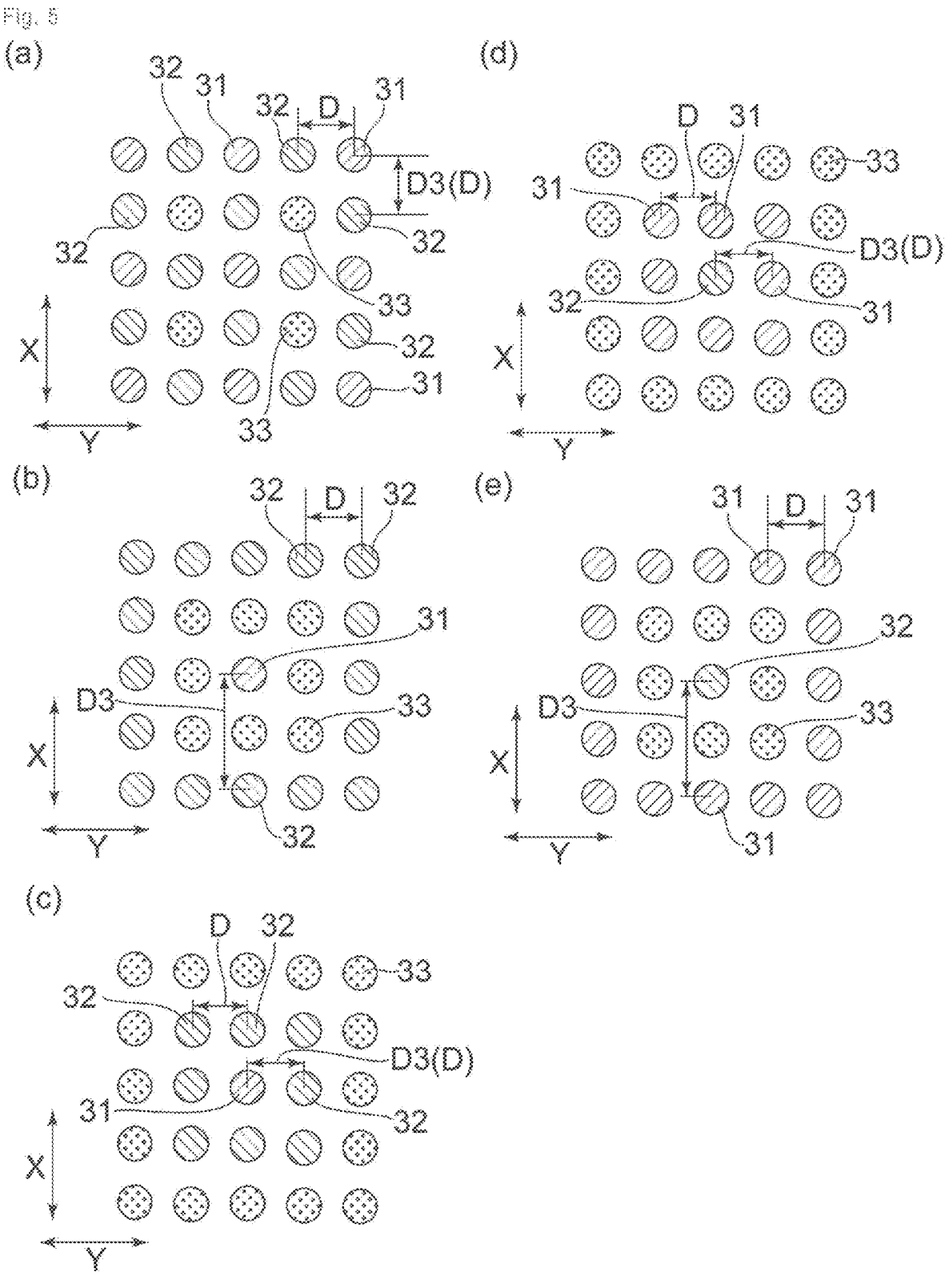
FIGS. 5(a) to 5(e) are plan views schematically showing arrangement patterns of the protrusion in the injection needle shown in FIG. 1.

For example, arrangement patterns shown in FIGS. 5(a), 5(b), and 5(e) include a first array arranged in the first direction X, a first array arranged in the second direction Y, and a first array arranged in a direction inclined with respect to both directions of the first direction X and the second direction Y, more specifically, arranged in a direction inclined at an angle of 45 degrees. Arrangement patterns shown in FIGS. 5(d) and 5(c) include a first array in which a plurality of protrusions, which are the first or second protrusions 31 or 32, are arranged between the third protrusions 33. Arrangement patterns shown in FIGS. 8(a) and 11(a) include a second array arranged in the first direction X and a second array arranged in the second direction Y. Arrangement patterns shown in FIGS. 8(c) and 11(b) include a second array arranged in the first direction X, a second array arranged in the second direction Y, and a second array arranged in a direction inclined with respect to both directions of the first direction X and the second direction Y, more specifically, arranged in a direction inclined at an angle of 45 degrees.

The plurality of first arrays or the second arrays are preferably present in the protrusion arrangement region, and are preferably present in a state of being dispersed in the plane direction of the protrusion arrangement region.

From the viewpoint of accurately controlling the insertion depth, it is also preferable to have an array (hereinafter, referred to as "third array") in which at least three or more third protrusions 33 are disposed so as to surround the periphery of the first protrusion 31 or the second protrusion 32, or an array (hereinafter, referred to as "fourth array") in which at least three or more protrusions, which are the second protrusions 32 or the third protrusions 33, are arranged so as to surround the periphery of the first protrusion 31. It is also preferable to have an array (hereinafter, referred to as "fifth array") in which at least three or more composite protrusions (composite first protrusion 51 or composite second protrusion 52) having the insertion depth controller are arranged so as to surround the periphery of the first protrusion 31 or the second protrusion 32 having no insertion depth controller.

The protrusion surrounded by the third protrusions 33 in the third array or the protrusion surrounded by the composite protrusions in the fifth array may be any one of only the first protrusion 31, only the second protrusion 32, or both the first protrusion 31 and the second protrusion 32. With respect to the third array or the fifth array, the number of protrusions surrounded by the third protrusion 33 or the composite protrusion is preferably 1 or more and 4 or less, and more preferably 1 or 2. With respect to the fourth array, the number of first protrusions 31 surrounded by the second or third protrusion 32 or 33 is preferably 1 or more and 10 or less, and more preferably 1 or more and 5 or less.

For example, the arrangement patterns shown in FIGS. 5(a), 5(b), and 5(e) include a third array in which the third protrusion 33 is surrounded by a single protrusion, which is the first or second protrusion 31 or 32. The arrangement patterns shown in FIGS. 5(c) and 5(d) include a third array in which the third protrusion 33 is surrounded by a plurality of protrusions, which are first or second protrusions 31 or 32.

The plurality of third arrays, the fourth arrays, or the fifth arrays are preferably present in the protrusion arrangement region, and are preferably present in a state of being dispersed in the plane direction of the protrusion arrangement region.

The arrangement pattern of the first protrusion 31, the second protrusion 32, and the third protrusion 33 may be, for example, as shown in FIG. 5(a) in which a pair of second protrusions 32, 32 are arranged with the first protrusion 31 interposed therebetween in the first direction X and the second direction Y and the third protrusions 33 may be arranged with the second protrusion 32 interposed therebetween in the first direction X or the second direction Y. Further, as shown in FIG. 5(b), the second protrusion 32 and the third protrusion 33 may be arranged to surround the periphery of the first protrusion 31, and the second protrusion 32 may be arranged outside the third protrusion 33. In addition, as shown in FIG. 5(c), the second protrusion 32 and the third protrusion 33 may be arranged to surround the periphery of the first protrusion 31, and the second protrusion 32 may be arranged inside the third protrusion 33. In addition, as shown in FIG. 5(d), the first protrusion 31 and the third protrusion 33 may be arranged to surround the periphery of the second protrusion 32, and the third protrusion 33 may be arranged outside the first protrusion 31. Further, as shown in FIG. 5(e), the first protrusion 31 and the third protrusion 33 may be arranged to surround the periphery of the second protrusion 32, and the third protrusion 33 may be arranged inside the first protrusion 31. In FIGS. 5(a) to 5(e), the first protrusion 31 is shown by hatching that is upward to the right, the second protrusion 32 is shown by hatching that is downward to the right, and the third protrusion 33 is shown by hatching of dots.

In a plan view of the sheet base 2, a distance D between tip ends of the protrusions adjacent to each other is preferably 0.01 mm or more, more preferably 0.02 mm or more, even more preferably 0.1 mm or more, and even more preferably more than 0.5 mm, from the viewpoint to reduce prevention of the first protrusion from being inserted due to the interference caused by the deformation of the skin when the adjacent protrusions are pressed against the skin.

Further, the distance D is preferably 10 mm or less, more preferably 5 mm or less, and even more preferably 3 mm or less, from the viewpoint that the blood flow improving effect induced by the adjacent protrusions can be obtained within the applicable range with no gap.

Further, the distance D is preferably 0.01 mm or more and 10 mm or less, more preferably 0.1 mm or more and 5 mm or less, and even more preferably more than 0.5 mm and 3 mm or less.

The adjacent protrusions are two protrusions with the shortest distance between vertices, and when one protrusion is surrounded by a plurality of other protrusions with the same distance between the protrusions, are the one protrusion and the other protrusion. The distance D is measured only using the first protrusion 31 and the second protrusion 32 as protrusions adjacent to each other. In other words, even when the third protrusion 33, the tip end surface of which is the insertion depth controller 40, exists, the distance D is measured without using the third protrusion 33.

A thickness T of the sheet base 2 of the injection needle 1A is preferably 5 μm or more, more preferably 10 μm or more, and even more preferably 20 μm or more.

Further, the thickness T is preferably 2 000 μm or less, more preferably 1 000 μm or less, and even more preferably 500 μm or less, from the viewpoint of facilitating the pressing of the injection needle 1A against the skin.

In addition, the thickness T is preferably 5 μm or more and 2 000 μm or less, more preferably 10 μm or more and 1 000 μm or less, and even more preferably 20 μm or more and 500 μm or less (see FIG. 1).

The thickness T of the sheet base 2 can be measured by the following method.

<Method of Measuring Thickness of Sheet Base>

The sheet base 2 of the injection needle 1A is observed using an SEM or a microscope in a state of being magnified by a predetermined magnification as shown in FIG. 1. Next, as shown in FIG. 1, a distance in a thickness direction Z of the sheet base 2 is measured from a surface on the side of the sheet base 2 where the protrusion protrudes to a surface opposite to the surface. The distance measured in this way is defined as a thickness T of the base portion.

The injection needle 1A may have only the first protrusion 31, but preferably has a plurality of first protrusions.

Further, the injection needle 1A preferably has a region in which the number N1 of the first protrusions 31 per 1 cm² or the number N2 of the second protrusions per 1 cm² is as follows when viewed in a plan view.

The number N1 of the first protrusions 31 or the number N2 of the second protrusion is preferably 1 or more, more preferably 5 or more, and even more preferably 10 or more, from the viewpoint of enabling efficient injection of the liquid.

Further, the number N1 of the first protrusions 31 or the number N2 of the second protrusion is preferably 400 or less, more preferably 300 or less, and even more preferably 200 or less, from the viewpoint of easily controlling the injection amount of the liquid and the injection range of the liquid.

In addition, the number N1 of the first protrusions 31 or the number N2 of the second protrusion is preferably 1 or more and 400 or less, more preferably 5 or more and 300 or less, and even more preferably 10 or more and 200 or less, from both of these viewpoints.

The injection needle 1A may have only the second protrusion, or may have a plurality of second protrusions but preferably has a plurality of first protrusions 31.

The injection needle 1A preferably has a region in which a total number N1+N2 of the first protrusions 31 and the second protrusions 32 per 1 cm² is as follows when viewed in a plan view.

The total number N1+N2 is preferably 2 or more, more preferably 5 or more, even more preferably 10 or more, even more preferably 20 or more, and even more preferably 30 or more, from the viewpoint of causing a flare reaction in the entire range to which the injection needle 1A is applied and facilitating the blood flow promoting effect and the viewpoint of enabling efficient injection of the liquid.

The total number N1+N2 is preferably 500 or less, more preferably 300 or less, even more preferably 200 or less, and even more preferably less than 200, from the viewpoint of easily controlling the injection amount of the liquid and the injection range of the liquid.

The total number N1+N2 is preferably 10 or more and 500 or less, more preferably 20 or more and 300 or less, and even more preferably 30 or more and less than 200, from both of these viewpoints.

A ratio N2/N1 of the number N2 of the second protrusions per 1 cm² to the number N1 of the first protrusions 31 per 1 cm² is preferably 0.01 or more, more preferably 0.1 or more, even more preferably 0.5 or more, even more preferably 1 or more, and even more preferably 2.4 or more. It is preferable from the viewpoint of efficiently causing a flare reaction around the first protrusion 31 through which the liquid is injected and obtaining the blood flow promoting effect. It is preferable also from the viewpoint of improving the injection probability by preventing the first protrusion 31 from not being inserted into the skin when the injection needle 1A is pressed against the skin.

The ratio N2/N1 is preferably 100 or less, more preferably 50 or less, and even more preferably 10 or less, from the viewpoint of enabling the insertion with a small insertion pressure and enabling the efficient injection of the liquid by reducing the amount of the liquid to be injected from one first protrusion.

The ratio N2/N1 is preferably 0.01 or more and 100 or less, more preferably 1 or more and 50 or less, and even more preferably 2.4 or more and 10 or less, from both of these viewpoints.

The number of first protrusions 31 per 1 cm² when the injection needle 1A is viewed in a plan view can be measured by the following method.

<Method of Measuring Number of First Protrusions Per 1 cm²>

The number of first protrusions 31 per 1 cm² can be calculated in a manner that the number (pieces) of the first protrusions 31 included in the protrusion arrangement region where a plurality of microprotrusions 3 are dispersed in a plane direction is divided by a total area (cm²) of the protrusion arrangement region. The total area of the protrusion arrangement region is an area of a region surrounded by a virtual line connecting vertices of the protrusions arranged on an outer edge of the region when the injection needle 1A is viewed in a plan view. When the number of protrusions of the injection needle 1A is 2 or less, the number of first protrusions 31 included in a square region of 1 cm-square can be measured by counting when the injection needle 1A is viewed in a plan view.

By using the injection needle of the present invention, it is possible to obtain the blood flow promoting effect in a wide range in which the first protrusion and the second protrusion are arranged, and to reliably inject the drug into the skin.

The inventors consider that the drug is injected into the skin and the blood flow is improved around the skin into which the drug is injected, whereby the drug can be easily absorbed by the skin, the drug capable of not being absorbed can be prevented from flowing out of the skin, and the effect of the drug can be easily obtained.

Next, another embodiment of an injection needle of the present invention will be described. In such an embodiment, only differences from the embodiment described above will be described, the description of the above-described embodiment will be appropriately applied unless otherwise particularly described, and the same members will be denoted by the same reference numerals. Examples are shown in FIGS. 6 to 8(c) and FIGS. 9 to 11(c).

An injection needle of the present invention preferably includes a composite first protrusion 51 in which the third protrusion and the insertion depth controller 40 are integrally formed in the direction of the sheet base of the first protrusion 31. An example of the injection needle (hereinafter, also referred to as "injection needle 1B") including the composite first protrusion 51 will be described. In the injection needle 1B, the first protrusion 31 is molded integrally with the insertion depth controller 40 on the outer periphery on the base side. More specifically, a diameter-expanded portion 41 is formed on the base side, and a step portion is formed at an upper end portion of the diameter-expanded portion 41 so as to overhang outward in a radial direction of the first protrusion 31. Then, the step portion is the insertion depth controller 40.

An overhang length L1 of the step portion of the composite first protrusion 51 is preferably 0.002 mm or more, and more preferably 0.01 mm or more, from the viewpoint of acting as a stopper for preventing the first protrusion 31 from being inserted more than necessary.

Further, the length L1 is preferably 2 mm or less, and more preferably 0.1 mm or less, from the viewpoint of improving the degree of density of the first protrusion 31 and the second protrusion 32 and obtaining the blood flow promoting effect in a wide range to which the microprotrusion implement is applied.

In addition, the length L1 is preferably 0.002 mm or more and 2 mm or less, and more preferably 0.01 mm or more and 0.1 mm or less.

Figure 6:
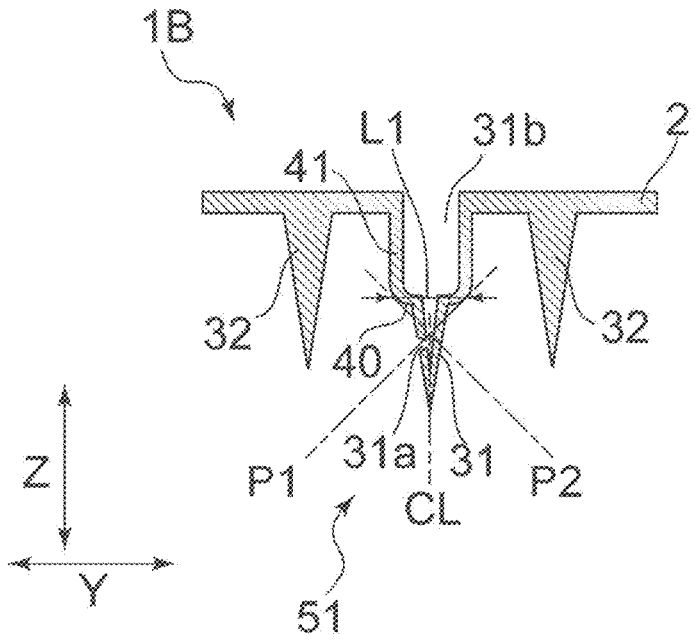
FIG. 6 is a cross-sectional view according to another preferred embodiment of the present invention, and is a view corresponding to FIG. 1.

The length L1 is a linear distance obtained by measuring a distance between an inner end portion and an outer end portion of the step portion along a plane orthogonal to the height direction, and is a distance between two contacts of each of the inner end portion and the outer end portion and each of tangent lines P1 and P2 forming 45° with respect to a center line CL of the first protrusion as shown in FIG. 6.

Figure 7:
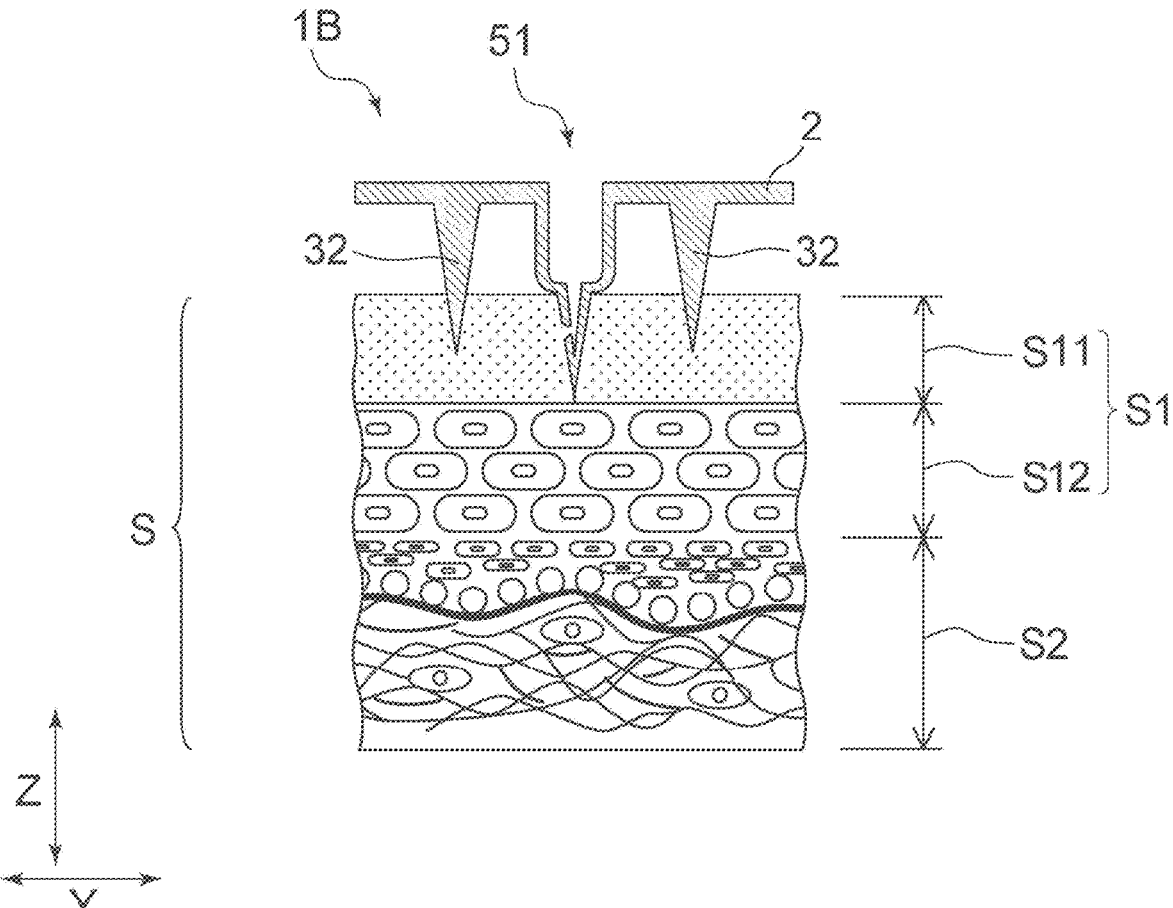
FIG. 7 is a diagram schematically showing a use state of the injection needle shown in FIG. 6, and is a diagram corresponding to FIG. 3.

Also in the injection needle 1B, when the composite first protrusion 51 and the second protrusion 32 are inserted into the skin from the tip end side, the insertion depth controller 40 comes into contact with the surface of the skin. Then, the insertion of the composite first protrusion 51 and the second protrusion 32 is stopped, and the composite first protrusion 51 and the second protrusion 32 are prevented from being inserted into a deeper site of the skin. In the composite first protrusion 51, since the insertion depth controller 40 is integrally formed around the first protrusion 31, the composite first protrusion 51 can be reliably prevented from being inserted into the deeper site of the skin. Such an example is shown in FIG. 7.

An arrangement pattern of the composite first protrusion 51 and the second protrusion 32 is not particularly limited. For example, as shown in FIG. 8(a), a pair of second protrusions 32, 32 may be arranged with the composite first protrusion 51 interposed therebetween in the first direction X and the second direction Y. Further, as shown in FIG. 8(b), the second protrusions 32 may be arranged so as to surround the periphery of the composite first protrusion 51. In addition, as shown in FIG. 8(c), the composite first protrusion 51 may be arranged so as to surround the periphery of the second protrusion 32. In FIGS. 8(a) and 8(b), the composite first protrusion 51 is shown by hatching that is upward to the right, and the second protrusion 32 is shown by hatching that is downward to the right.

Figure 9:
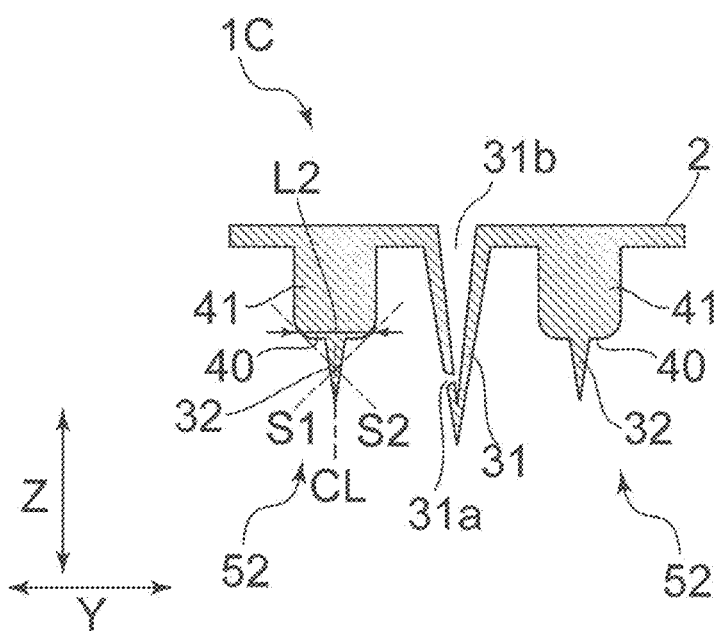
FIG. 9 is a cross-sectional view according to further another preferred embodiment of the present invention, and is a view corresponding to FIG. 1.

The injection needle of the present invention preferably includes a composite second protrusion 52 in which the insertion depth controller 40 is integrally formed around the second protrusion 32. An example of the injection needle (hereinafter, also referred to as "injection needle 1C") including the composite second protrusion 52 will be described. In the injection needle 1C, the second protrusion 32 is molded integrally with the insertion depth controller 40 on the outer periphery on the base side. More specifically, a diameter-expanded portion 41 is formed on the base side, and a step portion is formed at an upper end portion of the diameter-expanded portion 41 so as to overhang outward in a radial direction of the second protrusion 32. Then, the step portion is the insertion depth controller 40. Such an example is shown in FIG. 9.

An overhang length L2 of the step portion of the composite second protrusion 52 is preferably 0.002 mm or more, and more preferably 0.01 mm or more, from the viewpoint of acting as a stopper for preventing the second protrusion 32 from being inserted more than necessary.

Further, the length L2 is preferably 2 mm or less, and more preferably 0.1 mm or less, from the viewpoint of improving the degree of density of the first protrusion 31 and the second protrusion 32 and obtaining the blood flow promoting effect in a wide range to which the injection needle is applied.

In addition, the length L2 is preferably 0.002 mm or more and 2 mm or less, and more preferably 0.01 mm or more and 0.1 mm or less.

The length L2 can be measured by the same manner as the length L1.

Figure 10:
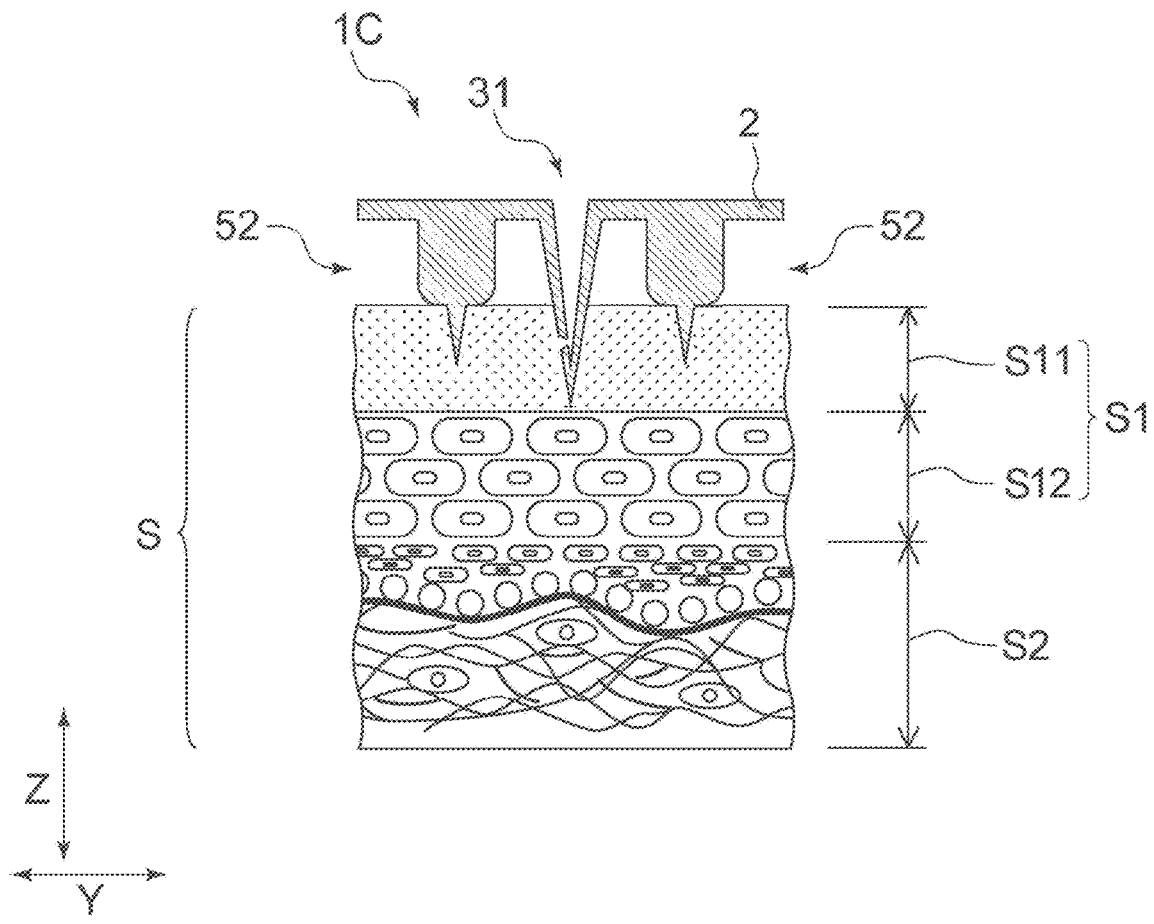
FIG. 10 is a diagram schematically showing a use state of the injection needle shown in FIG. 9, and is a diagram corresponding to FIG. 3.

Also in the injection needle 1C, when the first protrusion 31 and the composite second protrusion 52 are inserted into the skin from the tip end side, the insertion depth controller 40 comes into contact with the surface of the skin. Then, the insertion of the first protrusion 31 and the composite second protrusion 52 is stopped, and the first protrusion 31 and the composite second protrusion 52 are prevented from being inserted into a deeper site of the skin. In the composite second protrusion 52, since the insertion depth controller 40 is integrally formed around the second protrusion 32, the composite second protrusion 52 can be reliably prevented from being inserted into the deeper site of the skin. Such an example is shown in FIG. 10.

An arrangement pattern of the first protrusion 31 and the composite second protrusion 52 is not particularly limited. For example, as shown in FIG. 11(a), a pair of composite second protrusions 52, 52 may be arranged with the first protrusion 31 interposed therebetween in the first direction X and the second direction Y. Further, as shown in FIG. 11(b), the composite second protrusions 52 may be arranged so as to surround the periphery of the first protrusion 31. In addition, as shown in FIG. 11(c), the first protrusion 31 may be arranged so as to surround the periphery of the composite second protrusion 52. In FIGS. 11(a) and 11(b), the first protrusion 31 is shown by hatching that is upward to the right, and the composite second protrusion 52 is shown by hatching that is downward to the right.

Next, matters common to each of the above-described embodiments will be described.

The injection needle 1A, 1B, or 1C of each of the embodiments of the present invention preferably contains a thermoplastic resin from the viewpoint of ensuring the handling ability of the material, the strength and workability of the injection needle, and the hardness of the first protrusion 31 and the second protrusion 32 and obtaining the blood flow promoting effect together with facilitating the injection of the liquid. The injection needle is further preferably formed of the base sheet containing the thermoplastic resin.

The base sheet contains a thermoplastic resin as a main constituent material. The main constituent material means that the mass of the thermoplastic resin is 50% or more of the total mass of the base sheet of the microprotrusion implement, and the mass of the thermoplastic resin is more preferably 100%.

Examples of the thermoplastic resin include polyolefin, polyester, polyamide, polyamide-imide, polyether ether ketone, polyetherimide, polyvinyl chloride, acrylic resin, polystyrene resin, or combination thereof.

Examples of the polyolefin include polypropylene and polyethylene.

Examples of the polyester include polyethylene terephthalate, polyfatty acid ester, polylactic acid, polycaprolactone, and poly butylene succinate.

An example of the polyamide includes nylon.

From the viewpoint of biodegradability, polyfatty acid ester is preferably used. Specific examples of the polyfatty acid ester include polylactic acid, polyglycolic acid, or combinations thereof.

The ratio of the mass of the thermoplastic resin included in the injection needle 1A, 1B or 1C to the total mass of the injection needle 1A, 1B, or 1C is preferably 50% or more, more preferably 70% or more, and even more preferably 90% or more, from the viewpoint of improving moldability and dimensional stability of the injection needle.

Further, the mass ratio of the thermoplastic resin is preferably 100% or less, more preferably 98% or less, and even more preferably 96% or less, from the viewpoint of adding a functional agent to the injection needle to give various effects.

Further, the mass ratio of the thermoplastic resin is preferably 50% or more and 100% or less, more preferably 70% or more and 98% or less, and even more preferably 90% or more and 96% or less.

Here, as various functional agents, antibacterial agents, bactericidal agents, moisturizers, flow improvers, antistatic agents, and colorants can be used.

Although the present invention has been described based on the preferred embodiments, the present invention is not limited to the above-described embodiments and can be appropriately changed.

For example, in the first embodiment, the second protrusion 32 and the third protrusion 33 are solid, but the second protrusion 32 and the third protrusion 33 may be hollow. In the second embodiment, the composite second protrusion 52 is solid, but the composite second protrusion 52 may be hollow. In the injection needle 1A, 1B, or 1C, the protrusions other than the first protrusion 31 are preferably solid. Thus, the liquid to be discharged from the opening 31a of the first protrusion 31 can be prevented from being accumulated inside the other protrusions, and thus the liquid can be efficiently injected.

In the injection needles 1A to 1C, the protrusions are arranged in an array shape (single or a plurality of rows), but the plurality of protrusions may be an arbitrary arrangement such as an aligned arrangement so as to form an arbitrary annular shape, for example, a circular shape, an elliptical shape, a square shape, a rectangular shape, a hexagonal shape, or a star shape, in addition to the array shape.

In the injection needle 1A, the third protrusion 33 has the columnar shape, but the third protrusion 33 may be a truncated cone shape with a flat tip end or may be a conical shape with a curved tip end surface. In addition, the shape in plan view of the third protrusion 33 is not particularly limited, and may be a circular shape, an elliptical shape, a square shape, a rectangular shape, a hexagonal shape, or a star shape.

Further, the injection needle of the present invention may include the first protrusion 31, the second protrusion 32, the composite first protrusion 51, and the composite second protrusion 52, may include the first protrusion 31, the second protrusion 32, and the composite first protrusion 51, may include the first protrusion 31, the second protrusion 32, and the composite second protrusion 52, may include the first protrusion 31, the composite first protrusion 51, and the composite second protrusion 52, or may include the composite first protrusion 51 and the composite second protrusion 52.

In addition, the composite first protrusion 51 may be formed such that the insertion depth controller 40 is integrally formed around the plurality of first protrusions 31 as shown in FIG. 12(a). Further, the composite second protrusion 52 may be formed such that the insertion depth controller 40 is integrally formed around the plurality of second protrusions 32 as shown in FIG. 12(a).

Further, the second protrusion 32 may have a cut-out circular shape in cross-sectional view as shown in FIG. 12(b).

In addition, the injection needle of the present invention may have one first protrusion 31 and one second protrusion 32, or may have a plurality of first protrusions 31 and a plurality of second protrusions 32.

18

EXAMPLES

Examples of the present invention will be described in more detail below, but the present invention is not limited to these Examples.

Example 1

An injection needle having the same configuration as that of the injection needle 1A as shown in FIG. 1 and having the same arrangement as shown in FIG. 5(a) was manufactured. A dimension of each protrusion of the injection needle, a dimension of the sheet base, the number of first protrusions per 1 $cm^2$, a distance between tip ends of the adjacent first protrusions or second protrusions are as indicated in Table 1. The injection needle was formed by subjecting a base sheet made of 100% polylactic acid, which is a thermoplastic resin, to a protrusion forming process using a processing needle to which ultrasonic vibration was applied.

Example 2

An injection needle having the same configuration as that of the injection needle 1A as shown in FIG. 1 and having the same arrangement as shown in FIG. 5(d) was manufactured. It was the same as in Example 1 except that each element was as indicated in Table 1.

Example 3

An injection needle having the same configuration as that of the injection needle 1C as shown in FIG. 9 and having the same arrangement as shown in FIG. 11(a) was manufactured. It was the same as in Example 1 except that each element was as indicated in Table 1.

Example 4

An injection needle having the same configuration as that of the injection needle 1B as shown in FIG. 6 and having the same arrangement as shown in FIG. 8(a) was manufactured. It was the same as in Example 1 except that each element was as indicated in Table 1.

Example 5

An injection needle having the same configuration as that of the injection needle 1A as shown in FIG. 1 and having the same arrangement as shown in FIG. 14(a) was manufactured. It was the same as in Example 1 except that each element was as indicated in Table 1.

Example 6

An injection needle having the same configuration as that of the injection needle 1A as shown in FIG. 1 and having the same arrangement as shown in FIG. 14(b) was manufactured. It was the same as in Example 1 except that each element was as indicated in Table 1.

Example 7

An injection needle having the same configuration as that of the injection needle 1A as shown in FIG. 1 and having the same arrangement as shown in FIG. 14(c) was manufactured. It was the same as in Example 1 except that each element was as indicated in Table 1.

Comparative Example 1

An injection needle having a first protrusion 31 and a third protrusion 33 was manufactured (see FIGS. 13(a) and 13(b)). It was the same as in Example 1 except that each element was as indicated in Table 1 and the protrusions 31 and 33 were arranged as shown in FIG. 13(b).

[Evaluation of Flare Reaction]

A flare reaction of the injection needles of Examples 1 to 7 and Comparative Example 1 was evaluated by the following method.

Each of the injection needles of Examples 1 to 7 and Comparative Example 1 was attached to the skin of the subject, and pressed with a load of about 5 N for 10 seconds. After being pressed for 10 seconds, a microprotrusion implement was peeled off, the portion where the microprotrusion implement was pressed was observed with a microscope at a magnification of 30 times, and a range of the flare reaction was evaluated according to the following criteria. Evaluation results are indicated in Table 1.

A: Flare reaction occupied area being 70% or more

B: Flare reaction occupied area being 30% or more and less than 70%

C: Flare reaction occupied area being 10% or more and less than 30%

D: Flare reaction occupied area being 0% or more and less than 10%

The flare reaction occupied area was calculated by the following formula.

Flare reaction occupied area (%)=Area where flare reaction occurred/Area of protrusion arrangement region×100

The area of the protrusion arrangement region was defined as an area surrounded by the outermost protrusions 31, 32, and 33 included in the area.

[Evaluation of Drug Injectability]

Drug injectability of the injection needles of Examples 1 to 7 and Comparative Example 1 was evaluated by the following method.

Each the injection needles of Examples 1 to 7 and Comparative Example 1 was attached to a syringe (GASTIGHT #1710, manufactured by Hamilton Company), was inserted into the removed pig skin with momentum in a state of being tilted 10° from vertical with a load of 2 N or more, and a drug solution of 100 μL was injected at an injection rate of 1 μL/sec. After the injection, the syringe was removed from the pig skin, and the overflowing or leaking drug that did not enter the pig skin was wiped off with a waste cloth. A weight of the removed pig skin before and after the injection of the drug solution was measured, a weight difference from the pig skin before the injection of the drug solution was used as the injection amount of the drug solution, and the injection amount/dosage×100 was evaluated as an injection rate (%) according to the following criteria. Regarding the insertion depth of the injection needle, it was confirmed that the insertion of the first protrusion was suppressed by the insertion depth controller.

Evaluation results are indicated in Table 1.

A: Injection rate being 75% or more and 100% or less

B: Injection rate being 50% or more and less than 75%

C: Injection rate being 25% or more and less than 50%

D: Injection rate being 0% or more and less than 25%

TABLE 1

| | | | Example 1 | Example 2 | Example 3 | Example 4 | Example 5 | Example 6 | Example 7 | Comparative Example 1 |
|---|---|---|---|---|---|---|---|---|---|---|
| Dimension | First protrusion | Tip end diameter (μm) | 20 | 10 | 10 | 10 | 10 | 10 | 10 | 10 |
| | | Protrusion height H1 (μm) | 2000 | 2000 | 2000 | 2000 | 2000 | 2000 | 2000 | 2000 |
| | | Number N1 (pieces) of protrusions per 1 cm$^2$ | 25 | 3 | 144 | 144 | 5 | 11 | 4 | 58 |
| | Second protrusion | Tip end diameter (μm) | 150 | 150 | 150 | 150 | 150 | 150 | 150 | — |
| | | Protrusion height H2 (μm) | 1500 | 1500 | 1500 | 1500 | 1500 | 1500 | 1500 | — |
| | | Number N2 (pieces) of protrusions per 1 cm$^2$ | 33 | 22 | 133 | 133 | 20 | 99 | 10 | 0 |
| | | Number N1 + N2 (pieces) of protrusions per 1 cm$^2$ | 58 | 25 | 278 | 278 | 25 | 110 | 14 | 58 |
| | | Ratio N2/N1 of number N2 of second protrusions to number N1 of first protrusions per 1 cm$^2$ | 1.3 | 0.1 | 0.9 | 0.9 | 4.0 | 9.0 | 2.5 | 0.0 |
| | Puncture depth controller | Distance H3 (μm) from surface of sheet base to puncture depth controller | 900 | 900 | 900 | 900 | 900 | 900 | 900 | 900 |
| | | Difference H1-H3 (μm) between protrusion height of first protrusion and distance from surface of sheet base to puncture depth controller | 1100 | 1100 | 1100 | 1100 | 1100 | 1100 | 1100 | 1100 |
| | | Difference H2-H3 (μm) between protrusion height of second protrusion and distance from surface of sheet base to puncture depth controller | 600 | 600 | 600 | 600 | 600 | 600 | 600 | — |
| | | Difference H1-H2 (μm) between protrusion height of first protrusion and protrusion height of second protrusion | 600 | 600 | 600 | 600 | 600 | 600 | 600 | — |

TABLE 1-continued

| | | | Example 1 | Example 2 | Example 3 | Example 4 | Example 5 | Example 6 | Example 7 | Comparative Example 1 |
|---|---|---|---|---|---|---|---|---|---|---|
| | Distance D (mm) between tip ends of first and second protrusions adjacent to each other | | 1.50 | 1.50 | 0.75 | 0.75 | 2.23 | 1.50 | 5.00 | — |
| | Sheet base | Thickness (μm) | 400 | 400 | 400 | 400 | 400 | 400 | 400 | 400 |
| Test of skin | Evaluation of Hare reaction | | B | B | A | A | B | B | C | B |
| | Injectability of drug | | B | A | B | B | B | A | B | D |

As indicated in Table 1, in the injection needle of Comparative Example 1, the flare reaction was evaluated as B, but the drug injectability was evaluated as D. In other words, it can be seen that the injection needle of Comparative Example 1 can obtain a blood flow promoting effect, but is difficult to inject the liquid. In the injection needle of the Comparative Example 1, according to the evaluation of the drug injectability, because the insertion of the injection needle may have been insufficient, most of the drug leaked from the opening (drug solution injection portion) where the insertion was insufficient, and thus injection was difficult.

In contrast to the injection needle of Comparative Example 1, the injection needles of Examples 1 to 7 had a flare reaction being evaluated as A or B, and the drug injectability being evaluated as A, B or C. In other words, it can be seen that the injection needles of Examples 1 to 7 can easily inject the liquid and can obtain the blood flow promoting effect.

INDUSTRIAL APPLICABILITY

With the injection needle of the present invention, it is possible to control a depth of insertion into a skin, to inject a liquid, and to effectively promote a blood flow.

The invention claimed is:

1. An injection needle including:
protrusions, that protrude from a sheet base, the protrusions including:
a first protrusion having an opening at a tip end portion thereof and being hollow, and
a second protrusion having no opening at a tip end portion thereof; and
an insertion depth controller to control an insertion depth of the first protrusion, the insertion depth controller being at an intermediate position lower than a tip end position of the first protrusion and higher than a surface of the sheet base,
wherein the insertion depth controller is at a position lower than a tip end position of the second protrusion.

2. The injection needle according to claim 1, wherein the insertion depth controller controls the insertion depth of the first protrusion.

3. The injection needle according to claim 1, wherein a difference in height between the tip end position of the first protrusion and the position of the insertion depth controller is 1 μm or more and 5,000 μm or less.

4. The injection needle according to claim 1, wherein the first protrusion has a height higher than a height of the second protrusion.

5. The injection needle according to claim 1, wherein the first protrusion is a composite protrusion in which the insertion depth controller is integrally formed around the first protrusion.

6. The injection needle according to claim 1, wherein the second protrusion is a composite protrusion in which the insertion depth controller is integrally formed around the second protrusion.

7. The injection needle according to claim 1,
wherein the protrusions protruding from the sheet base include a third protrusion arranged around the first protrusion or the second protrusion, and
wherein the third protrusion has a tip end surface that is the insertion depth controller.

8. The injection needle according to claim 1, wherein the protrusions other than the first protrusion are solid.

9. The injection needle according to claim 1, wherein the injection needle contains a thermoplastic resin.

10. The injection needle according to claim 1, wherein the opening of the first protrusion is not formed at a tip of the first protrusion, but is formed at a lateral side of the first protrusion.

11. The injection needle according to claim 1, wherein a tip end diameter of the first protrusion is 1 μm or more and 300 μm or less.

12. The injection needle according to claim 1, wherein a tip end diameter of the second protrusion is equal to or more than the tip end diameter of the first protrusion.

13. The injection needle according to claim 1, wherein the injection needle includes a plurality of the first protrusions and a plurality of the second protrusions.

14. The injection needle according to claim 1, wherein a pair of the second protrusions are arranged with the first protrusion interposed therebetween.

15. The injection needle according to claim 1,
wherein the protrusions protrude from a first side of the sheet base, and
wherein a second side of the sheet base opposite the first side is free of any protrusions.

16. The injection needle according to claim 1,
wherein a tip of the first protrusion forms a first point,
wherein a tip of the second protrusion forms a second point different from the first point,
wherein a tip end portion of the insertion depth controller has a rounded portion,
wherein the second protrusion has a solid inner volume, and
wherein the tip end portion of the insertion depth controller is lower than the tip end position of the second protrusion.

17. The injection needle according to claim 1,
wherein an end of the first protrusion opposite the tip end portion, at the sheet base, has an opening, at a second side of the sheet base opposite a first side of the sheet base from which the protrusions protrude,
wherein the second side of the sheet base is free of any openings except for the opening formed at the end of the first protrusion at the second side of the sheet base, and

wherein all of the protrusions, including the first protrusion and the second protrusion, are hollow.

18. The injection needle according to claim 1, wherein the injection needle is provided to inject a drug, where the second protrusion is to induce immunity by stimulation and the first protrusion is to inject the drug.

19. An injection needle arrangement comprising:

a plurality of protrusions, that protrude from a first side of a sheet base, the plurality of protrusions including:

a first protrusion having an opening at a tip end portion thereof and being hollow, a second protrusion having no opening at a tip end portion thereof; and an insertion depth controller in the form of one or more third protrusions to control an insertion depth of the first protrusion, wherein each of the one or more third protrusions has a tip end at a position lower than a tip end position of the first protrusion and a tip end position of the second protrusion and higher than a surface of the sheet base.

20. The injection needle arrangement according to claim 19, wherein a tip end portion of each of the one or more third protrusions is rounded, wherein a tip end of the first protrusion forms a first point, and wherein a tip end of the second protrusion forms a second point different from the first point.

\*    \*    \*    \*    \*

24